US 6,684,093 B2

(12) United States Patent
Kuth

(10) Patent No.: US 6,684,093 B2
(45) Date of Patent: Jan. 27, 2004

(54) MEDICAL DIAGNOSIS APPARATUS WITH PATIENT RECOGNITION

(75) Inventor: Rainer Kuth, Herzogenaurach (DE)

(73) Assignee: Siemens Aktiengesellschaft, Münich (DE)

(*) Notice: Subject to any disclaimer, the term of this patent is extended or adjusted under 35 U.S.C. 154(b) by 0 days.

(21) Appl. No.: 09/955,443

(22) Filed: Sep. 18, 2001

(65) Prior Publication Data

US 2002/0065457 A1 May 30, 2002

(30) Foreign Application Priority Data

Sep. 18, 2000 (DE) .......................... 100 46 110

(51) Int. Cl.$^7$ ............................... A61B 5/05
(52) U.S. Cl. ................. 600/407; 382/100; 382/115; 382/117; 382/124; 382/128
(58) Field of Search ................. 600/407, 300; 382/115–117, 128, 100; 705/3

(56) References Cited

U.S. PATENT DOCUMENTS

| | | | | | |
|---|---|---|---|---|---|
| 4,121,574 A | * | 10/1978 | Lester | ........................ | 600/479 |
| 4,156,230 A | * | 5/1979 | Riganati et al. | ............ | 382/124 |
| 5,071,168 A | * | 12/1991 | Shamos | ...................... | 283/117 |
| 5,325,294 A | * | 6/1994 | Keene | ............................ | 705/3 |
| 5,697,376 A | * | 12/1997 | Nomura et al. | ............. | 600/300 |
| 5,876,926 A | * | 3/1999 | Beecham | ....................... | 435/5 |
| 6,081,607 A | * | 6/2000 | Mori et al. | .................. | 382/110 |
| 6,173,068 B1 | * | 1/2001 | Prokoski | ..................... | 382/115 |
| 6,396,937 B2 | * | 5/2002 | Chen et al. | ................. | 382/100 |
| 6,406,426 B1 | * | 6/2002 | Reuss et al. | ................ | 600/300 |
| 6,542,627 B1 | * | 4/2003 | Kawata | ....................... | 382/128 |

FOREIGN PATENT DOCUMENTS

DE        39 43 097         7/1991
DE        40 09 051         1/1992

OTHER PUBLICATIONS

Williams, J.D., Use of Biometrics and Biomedical Imaging in Support of Battlefield Diagnosis, Fusion'98—First International Conference on Multisource–Multisensor Information Fusion, Las Vegas, Jul. 6–9, 1998.*

Baldwin, F.D., Believing in Biometrics: Biometric technologies not only exist—they work and are now affordable. Health Informatics, Aug. 2000, p. 37–46.*

MedPixTM Teaching File and Image Data Base, Case Inventory No. 593/1112 (May 15, 2000) Retrieved Nov. 22, 2002: URL <http://rad.usuhs.mil/synapse/radpix.html?mode=quiz&imid=593&quiz=yes&th=1&table=card&showall=#pic>.*

Smith, JP, "Authentication of digital medical images with digital signature technology" Radiology, vol. 194, 771–774, 1995.*

Anand, D and Niranjan, UC, Watermarking medical images with patient information Proced 20th Annual International Conference IEEE Engineering in Medicine and Biology Society, vol. 20, No. 2, 1998.*

Anand et al. Watermarking Medical Images with Patient Information. Proc. 20th Ann. Int. Conf. IEEE Engineering in Medicine and Biology Society, vol. 20, No. 2, 1998.*

* cited by examiner

*Primary Examiner*—George Manuel
*Assistant Examiner*—Barry Pass
(74) *Attorney, Agent, or Firm*—Schiff Hardin & Waite

(57) ABSTRACT

Medical diagnosis apparatuses (and a respective method for using such apparatuses) are provided, particularly large apparatuses operated in a centralized manner, (e.g., MR scanners, CT tomographs or the like), characterized by a patient acquisition device assigned to it for acquiring individual distinctive identification features of the patient, which are automatically stored with the apparatus data obtained.

10 Claims, 2 Drawing Sheets

MEDICAL DIAGNOSIS APPARATUS WITH PATIENT RECOGNITION

BACKGROUND OF THE INVENTION

1. Field of the Invention

The invention relates to a medical diagnosis apparatus, particularly large apparatuses operated in a centralized manner, such as MR scanners, CT tomographs or the like.

2. Description of the Related Art

Large medical apparatuses, due to their high costs, are usually operated by specialists to whom patients are referred from other doctors or, in clinics, from other departments. This situation can produce a problem of reliably assigning the patient to his data which are obtained during the examination or therapy in the large medical apparatus, since experience shows the repeated occurrence of an incorrect name preventing the correct assignment of the data to the respective patient. A simple typographical error when entering the patient's data is often all that is necessary to bring about such an incorrect assignment.

SUMMARY OF THE INVENTION

The invention is therefore based on the object of configuring a medical diagnosis apparatus of the type mentioned above in such a way that these types of mistakes and incorrect assignment of the diagnosis data to the respective patient are prevented from the outset.

In order to achieve this object, the invention provides for a medical diagnosis apparatus to be characterized according to the invention by a patient acquisition device assigned to it. This patient acquisition device is used for acquiring individual distinctive identification features of the patient which are automatically stored with the apparatus data obtained.

In this case, in a refinement of the invention, reliable assignment of the apparatus data obtained to the respective patient, which (even when other details, for example the patient's name, are entered erroneously) enables exact checking and correction at any time with the aid of the patient acquisition device according to the invention. The patient, and the respective information, is additionally protected particularly against operating errors, when, in a refinement of the invention, the medical diagnosis apparatus is disabled if the patient acquisition device is not actuated, and is enabled for the examination only by the actuation of the patient acquisition device. In this case, by way of example, fingertip sensors or else iris measuring devices are suitable as the patient acquisition device, since a fingerprint and also an iris measurement capture very reliable individual identifying characteristics of a patient, so that mistakes can be completely precluded.

In an especially advantageous manner, a camera, particularly a digital camera, may be provided as the patient acquisition device. In the case of such a digital camera, a safeguard device with plausibility comparison structures may additionally be connected downstream of this camera in order to be able to automatically clarify whether the photograph was successful.

Thus, by way of example, a comparison with typical facial contours, including the position of the two eyes, a nose and the mouth, can be used as a comparison criterion in order to be able to ascertain automatically, and without an operator first having to inspect the photograph, whether the patient's head was actually captured, or whether the camera was incorrectly oriented and simply photographed only the table or the floor. More exact checks are not even necessary since the invention deals only with correcting operating errors and inadvertent erroneous entries, and not with deliberate incorrect entries.

A real world application does not involve the situation where somebody lays a different person on the patient table during the process of acquisition with the digital camera and causes him to be photographed as the actual patient or manipulates him in some other way with the aid of a device used for deceptive intent. Thus, a plausibility assessment of the image from the digital camera in the manner described above is entirely sufficient for automatically protecting the actual recording. With the creation of the photograph or the actuation of the respective other patient acquisition device, the actual medical diagnosis apparatus is enabled. This ensures that firstly the patient acquisition data are stored on the respective data carrier on which the apparatus data (e.g., the image sets of a magnetic resonance scanner) are then stored.

DESCRIPTION OF THE DRAWINGS

Further advantages, features and details of the invention are provided from the following description of an exemplary embodiment and also with reference to the drawings.

DETAILED DESCRIPTION OF THE INVENTION

Figure 1:
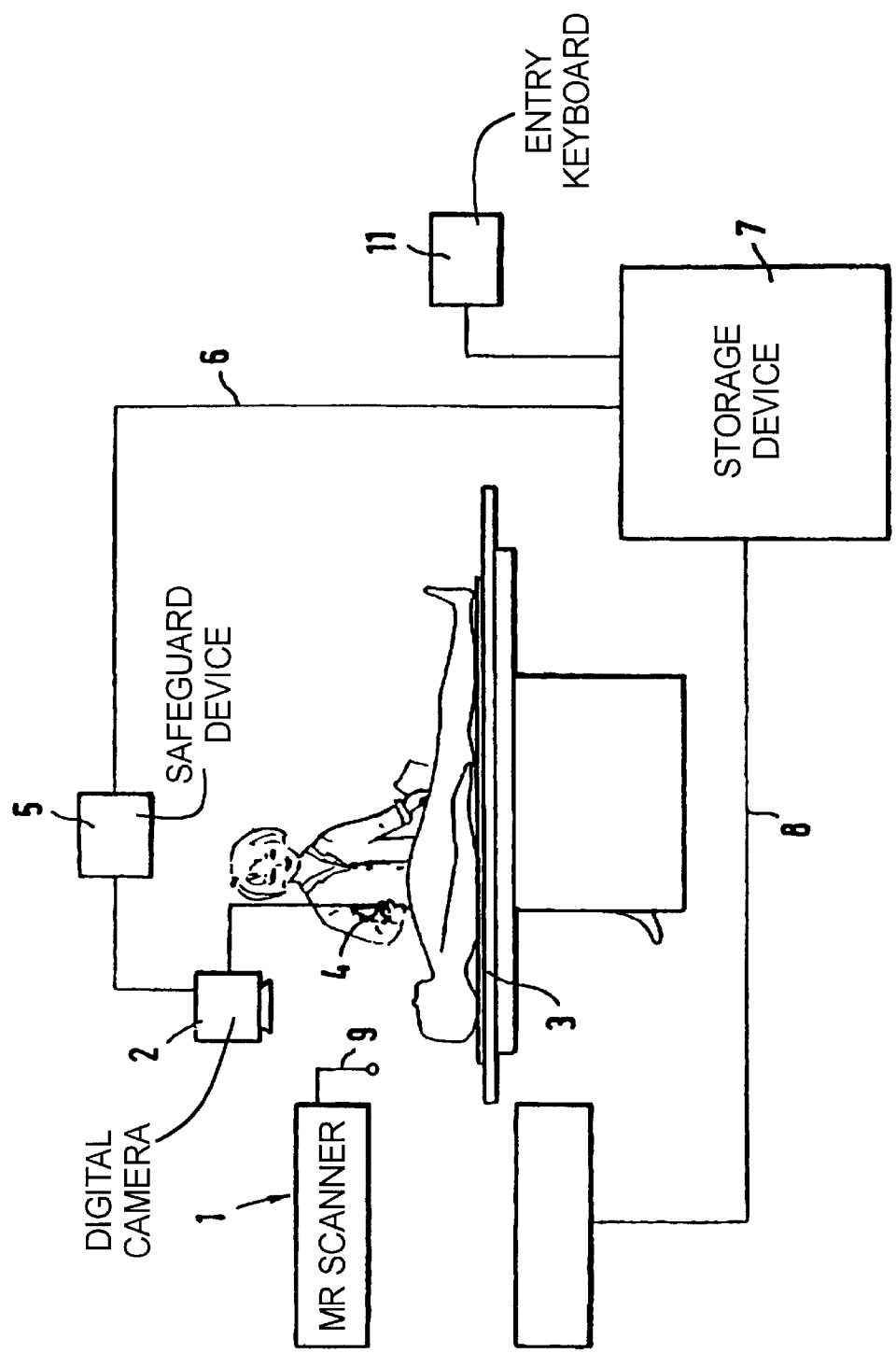
FIG. 1 is a diagrammatic picture showing an MR scanner according to the invention.

FIG. 1 diagrammatically shows a medical diagnosis device, specifically an MR scanner 1, with a patient acquisition device, specifically a digital camera 2, assigned to it. In the example shown in FIG. 1, the camera is arranged above the patient's couch/table 3 in the region of insertion into the MR scanner 1, although the position of some other patient acquisition device, such as a fingertip sensor or iris measuring device, could be appropriately located by a practitioner. Before the patient is inserted into the MR scanner 1, the digital camera 2 or other patient acquisition device is activated with the aid of its release 4 and the device (e.g., camera) creates a digital passport photograph (or other digital signature) of the patient. This data (e.g., photograph) is examined in a downstream safeguard device 5 with the aid of plausibility comparison structures to determine whether the image was actually successful, i.e., whether a human face or other characteristic can actually be recognized on the image. In the affirmative case, the image is forwarded via the data cable 6 to the acquisition and storage device 7, where it is printed at the top of the same data carrier which is also intended to hold the MR images. With the release of the digital image by the safeguard device 5, the MR scanner 1 is enabled via its data line 8, so that only then can the MR image sequences of the patient introduced into the MR scanner 1 actually be recorded with the aid of the scanner release 9.

Figure 2:
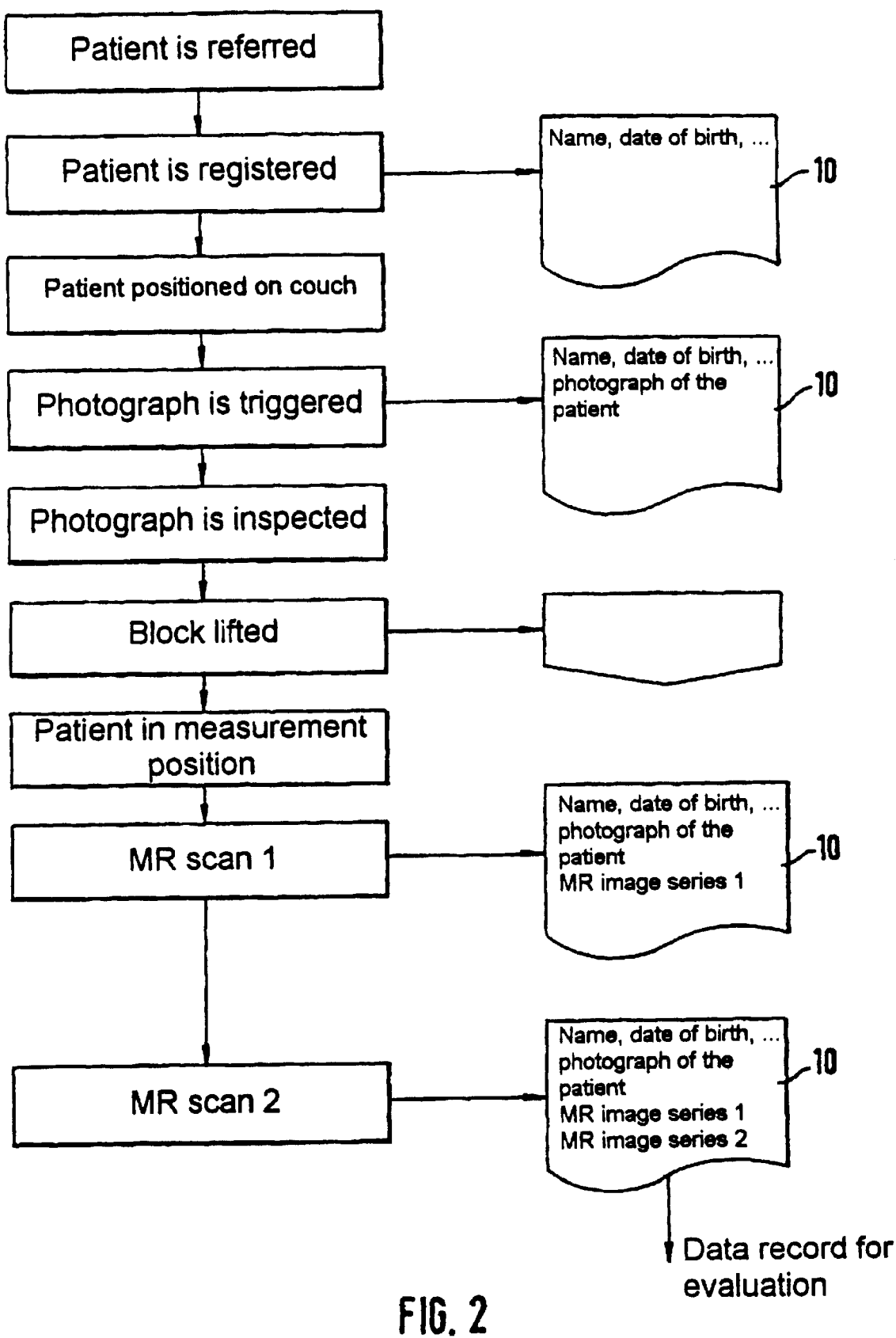
FIG. 2 is a flowchart of an examination procedure with the aid of the system according to the invention as shown in FIG. 1.

The flow diagram of FIG. 2 shows in detail how the various method steps take place using the system according to FIG. 1.

According to FIG. 2, the patient's data are initially acquired via an input device such as an entry keyboard 11 and printed on the data carrier 10 in the acquisition and storage device. Then, the patient's photograph is stored before the patient inserted in the measurement position can be examined with the aid of the MR scanner (this occurs, after the plausibility check of the photograph and the releasing of the block of the diagnosis apparatus). The individual image series during the examinations are applied to the data carrier 10 directly after the patient's photograph.

The patient acquisition device according to the invention, which could also comprise fingertip sensors or iris measuring devices or the like, automatically ensures that the apparatus data obtained can be unmistakably associated with the respective patient and assigned to the latter, even if errors have occurred during the entry of name, date of birth and the like. The photograph or the fingerprint allow reliable assignment in any case.

The above-described apparatus and method are illustrative of the principles of the present invention. Numerous modifications and adaptations will be readily apparent to those skilled in this art without departing from the spirit and scope of the present invention.

What is claimed is:

1. A medical diagnosis system, comprising:
   a medical diagnostic imaging apparatus configured to record diagnostic image data results of a patient obtained from said medical diagnostic imaging apparatus on a medical data storage medium;
   a biometric data recorder assigned to said medical diagnostic imaging apparatus configured to automatically acquire individual distinctive biometric identification data of a patient; and
   a recording mechanism configured to contemporaneously record and combine said individual distinctive biometric identification data with said diagnostic image data results on said medical data storage medium during an examination.

2. The medical diagnosis system as claimed in claim 1, wherein said medical diagnostic imaging apparatus is a large apparatus operated in a centralized manner selected from the group consisting of an MR scanner and a CT tomograph.

3. The medical diagnosis system as claimed in claim 1, further comprising an actuation mechanism of said biometric data recorder, said biometric data recorder being connected to said medical diagnostic imaging apparatus that permits use of said medical diagnosis apparatus only after actuation of said biometric data recorder device.

4. The medical diagnosis system as claimed in claim 1, wherein said biometric data recorder comprises a fingertip sensor.

5. The medical diagnosis system as claimed in claim 1, wherein said biometric data recorder comprises an iris measuring device.

6. The medical diagnosis system as claimed in claim 1, wherein said biometric data recorder comprises a camera.

7. The medical diagnosis system as claimed in claim 6, wherein said camera is a digital camera.

8. The medical diagnosis system as claimed in claim 1, further comprising a safeguard device with plausibility comparison structures that is connected downstream of said biometric data recorder permitting ascertainment of whether said individual distinctive biometric identification data acquisition was successful.

9. A method for performing a medical diagnosis, comprising:
   providing a medical diagnostic imaging apparatus;
   providing a biometric data recorder assigned to said medical diagnostic imaging apparatus;
   automatically recording individual distinctive biometric data of a patient with said biometric data recorder on a medical data storage medium;
   recording diagnostic image data results of said patient with said medical diagnostic imaging apparatus contemporaneously with said automatic recording of said individual distinctive biometric data during an examination; and
   combining said individual distinctive biometric data and said diagnostic image data results on said medical data storage medium contemporaneously with said recording during said examination.

10. A method for performing a medical diagnosis, comprising:
    providing a medical diagnostic imaging apparatus;
    providing a biometric data recorder assigned to said medical diagnostic imaging apparatus;
    automatically recording individual distinctive biometric data of a patient with said biometric data recorder on a medical data storage medium;
    positioning said patient on a couch or table; and
    acquiring a digital signature of an individual distinctive biometric feature related to said individual distinctive biometric data of said patient prior to recording diagnostic image data results;
    inspecting said digital signature;
    recording diagnostic image data results of the patient with said medical diagnostic imaging apparatus contemporaneously with said automatic recording of said individual distinctive biometric data during an examination only if said digital signature matches previously recorded data for said biometric feature stored on said medical data storage medium; and
    combining said individual distinctive biometric data and said diagnostic image data results on a medical data storage medium contemporaneously with said recording during said examination.

* * * * *